US00PP28980P2

(12) United States Plant Patent
Van Swieten

(10) Patent No.: US PP28,980 P2
(45) Date of Patent: Feb. 20, 2018

(54) *PHALAENOPSIS* ORCHID PLANT NAMED 'PHALDRIDOP'

(50) Latin Name: ***Phalaenopsis* hybrid**
Varietal Denomination: PHALDRIDOP

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 8 days.

(21) Appl. No.: 15/330,024

(22) Filed: Jul. 27, 2016

(51) Int. Cl.
*A01H 5/02* (2006.01)

(52) U.S. Cl.
USPC ..... Plt./311

(58) Field of Classification Search
USPC ..... Plt./311
See application file for complete search history.

(56) References Cited

PUBLICATIONS

UPOV-PLUTO: Plant Variety Database, citation for 'PHALDRIDOP'; Internet retrieval Sep. 25, 2017.*
EU Community Plant Variety Rights Application No. 2016/0955, Application n°A201600634, filed Apr. 18, 2016, 8 pages.
EU Community Plant Variety Office Official Gazette, 3.2016, Jun. 15, 2016, cover page and pp. 35, 52.

* cited by examiner

*Primary Examiner* — Susan McCormick Ewoldt
(74) *Attorney, Agent, or Firm* — Jondle & Associates, P.C.

(57) ABSTRACT

A new and distinct variety of *Phalaenopsis* plant named 'PHALDRIDOP', particularly characterized by having small, white flowers, 1 to 3 peduncles that are medium-long and sturdy, leaves that are oblong, and is propagated by meristem tissue culture, is disclosed.

3 Drawing Sheets

Genus and species: *Phalaenopsis* hybrid.
Variety denomination: 'PHALDRIDOP'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALDRIDOP'.

The new *Phalaenopsis* plant is a product of a planned breeding program conducted by the inventor in Bleiswijk, The Netherlands. The objective of this breeding program was to create a new *Phalaenopsis* plant with numerous attractive and unique small white flowers, suitable for potted plant production.

The new *Phalaenopsis* plant 'PHALDRIDOP' is a result of cross-pollination made by the inventor in April 2005 in Bleiswijk, The Netherlands of the proprietary female, or seed parent, *Phalaenopsis* hybrid '22819-01' (unpatented) with the proprietary male, or pollen parent, *Phalaenopsis* hybrid '01-1696' (unpatented).

The new *Phalaenopsis* was selected by the inventor as a single plant within the progeny of the stated cross-pollination in a controlled greenhouse in Bleiswijk, The Netherlands in July 2008. Asexual reproduction of the new *Phalaenopsis* plant by meristem tissue culture since 2011 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Apr. 18, 2016. 'PHALDRIDOP' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands and can be used to distinguish 'PHALDRIDOP' as a new and distinct variety of *Phalaenopsis* plant.

1) Small, white flowers;
2) 1 to 3 peduncles;
3) Peduncle is medium-long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs were taken in a greenhouse in Bleiswijk, The Netherlands, from 50-week old plants in June 2016. Colors in the photographs may differ from the color values cited in the detailed botanical description, which accurately describe the actual colors of the new variety.

DESCRIPTION OF THE NEW VARIETY

Figure 1:
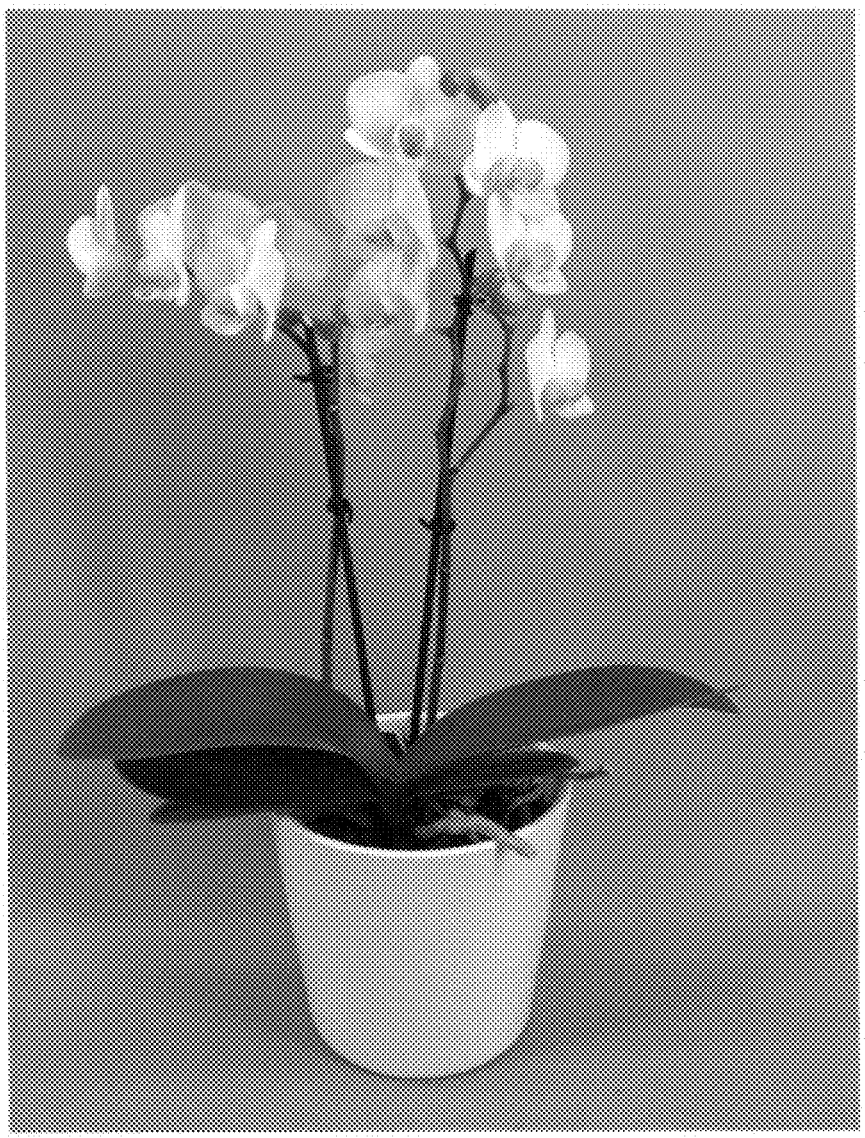
FIG. 1 shows the overall plant habit, including blooms, buds and foliage of 'PHALDRIDOP'.
Figure 2:
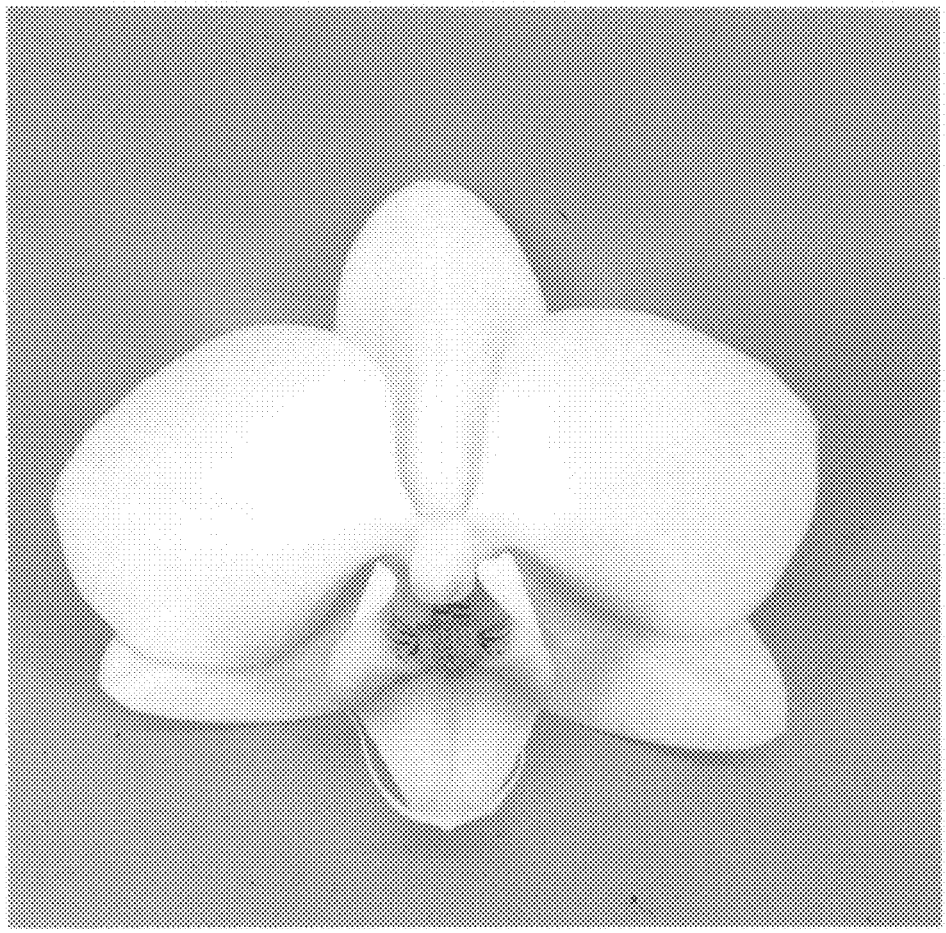
FIG. 2 shows a close-up of a flower of 'PHALDRIDOP'.
Figure 3:
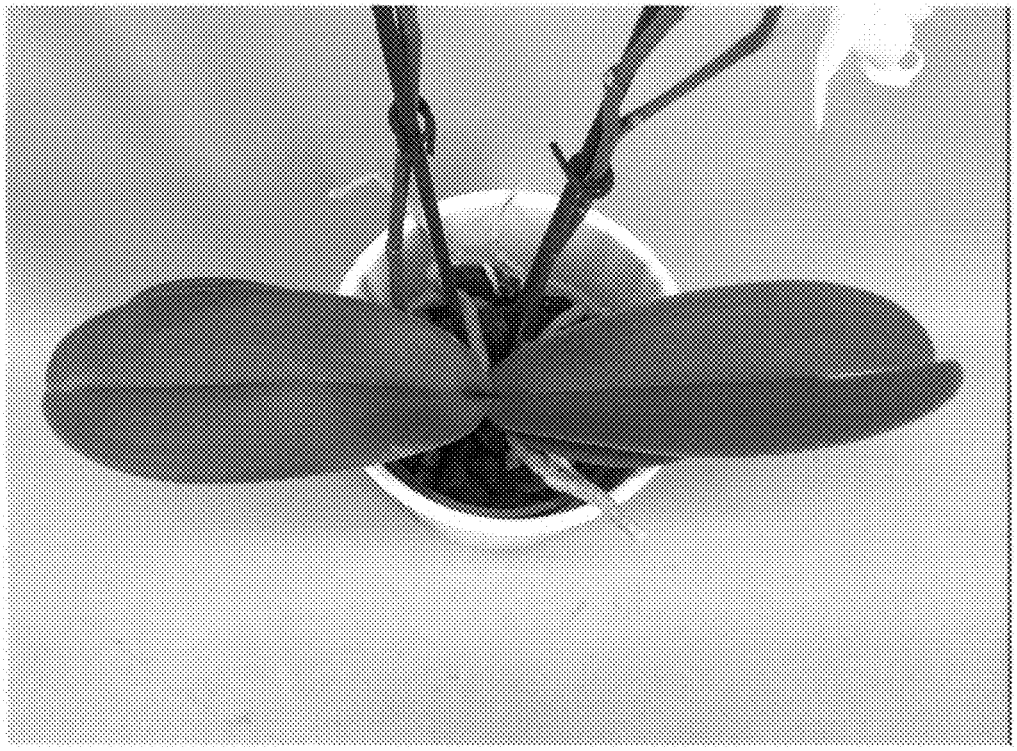
FIG. 3 shows a close-up of the leaves of 'PHALDRIDOP'.

The following detailed description sets forth the distinctive characteristics of 'PHALDRIDOP'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in June 2016 on 50-week old plants which were planted from a nursery tray in 12 centimeter, (diameter) pots and grown in a greenhouse between 27° C. to 29° C. for 30 weeks, continued by a cooling period of 8 weeks between 18° C. to 20° C. and 12 weeks in a greenhouse of 21° C.

DETAILED BOTANICAL DESCRIPTION

Classification:
- *Family*.—Orchidaceae.
- *Botanical*.—*Phalaenopsis* hybrid.
- *Common name*.—Moth orchid.
- *Variety name*.—'PHALDRIDOP'.

Parentage:
- *Female parent*.—*Phalaenopsis* cultivar '22819-01' (unpatented).
- *Male parent*.—*Phalaenopsis* cultivar '01-1696' (unpatented).

Propagation:
- *Type*.—Meristem tissue culture.

Roots:
- *Root description*.—Greyed-green colored roots with branching lateral roots having light purple colored root tips.

Plant:
- *Commercial crop time to flowering*.—Approximately 48 to 50 weeks from a rooted cutting to finish in a 12 cm pot.
- *Growth habit of peduncle*.—Standard, green leaves, raceme to panicle.
- *Height (from soil level to top of inflorescence)*.—Approximately 30.0 cm to 40.0 cm.
- *Width (measured from leaf tips)*.—About 30.0 cm to 34.0 cm.
- *Vigor*.—Moderate.

Leaves:
- *Mature leaves*.—Quantity per plant: 6 to 8 leaves are produced before flowering. Length (fully expanded): 15.0 cm to 18.0 cm. Width: 7.0 cm to 8.0 cm. Shape: Oblong. Base shape: Moderately elongated. Apex: Rounded unequal. Leaf blade angle with the petiole (measured from the horizontal position): Between 0 degrees and 30 degrees. Leaf margin: Entire. Color: Upper surface: RHS 146A. Lower surface: RHS 146B. Texture: Rough. Thickness: 2.1 mm to 2.4 mm. Venation: Pattern: Parallel. Color of the midvein: Upper surface: RHS 146A. Lower surface: RHS 146B.

Peduncle:
- *Quantity per plant*.—1 to 3.
- *Number of flowers per peduncle*.—16 to 22.
- *Length*.—30.0 cm to 40.0 cm.
- *Diameter*.—4.5 mm to 4.8 mm.
- *Strength*.—Sturdy.
- *Aspect*.—Upright to slightly pendant.
- *Texture*.—Slightly rough.
- *Color*.—Mix of light green (RHS 144A) and light brown (RHS 177A).
- *Internode length*.—4.0 cm to 4.5 cm.
- *Callosities*.—None.

Inflorescence description:
- *Appearance*.—Upright to slightly pendant, raceme to panicle inflorescence with bilaterally symmetrical flowers that open in succession beginning with the lowermost flower.
- *Inflorescence size*.—Height (from base to tip): 160.0 mm to 180.0 mm.
- *Flowering time*.—First flowers can be expected 10 to 11 months after planting in a 12 cm (diameter) pot.
- *Flower*.—Height: 50.0 mm to 52.0 mm. Diameter: 63.0 mm to 65.0 mm. Depth of lip: 17.0 mm to 19.0 mm.
- *Flower longevity*.—On the plant: 10 to 15 weeks.
- *Fragrance*.—Absent.
- *Flower bud*.—Length: 19.0 mm to 21.0 mm. Width: 14.0 mm to 16.0 mm. Shape: Egg shaped. Color: Light green (RHS 145C) and diluted purple (RHS 183B).
- *Petals*.—Arrangement: Open/free. Shape: Semi-circular. Apex: Obtuse asymmetric. Margin: Entire. Length (from base to tip): 29.0 mm to 31.0 mm. Width: 31.0 mm to 33.0 mm. Color (when fully opened): Upper surface: Basic color: White (RHS N155C). Over color: Absent. Lower surface: Basic color: White (RHS N155C). Over color: Slightly light purple in the middle (RHS 76C).
- *Dorsal sepal*.—Shape: Elliptic. Apex: Rounded. Margin: Entire. Length (from base to tip): 29.0 mm to 31.0 mm. Width: 18.0 mm to 20.0 mm. Color (when fully opened): Upper surface: Basic color: White (RHS N155C). Over color: Absent. Lower surface: Basic color: White (RHS N155C). Over color: Slightly light purple in the middle (RHS 76C).
- *Lateral sepals*.—Shape: Ovate. Apex: Obtuse asymmetric. Margin: Entire. Length (from base to tip): 29.0 mm to 31.0 mm. Width: 19.0 mm to 21.0 mm. Color (when fully opened): Upper surface: Basic color: White (RHS N155C). Over color: Absent. Lower surface: Basic color: White (RHS N155C). Over color: Light purple (RHS 76C).
- *Labellum (lip)*.—Margin: Entire. Whiskers: Present. Length of whiskers: 11.0 mm to 13.0 mm. Color of whiskers: White (RHS NN155C). Pubescence on the lip: Absent.
- *Lateral lobe*.—Shape: Spatulate. Length (from base to tip): 17.0 mm to 19.0 mm. Width: 12.0 mm to 14.0 mm. Color: White (RHS NN155C) with yellow on one side (RHS 7A) and a few brown stripes at the base (RHS 172B).
- *Apical lobe*.—Shape: Triangular. Length: 16.0 mm to 18.0 mm. Width: 18.0 mm to 20.0 mm. Color: White (RHS NN155C) with yellow at the base (RHS 7A).

*Callus*.—Average size: Small to medium. Height: 0.5 cm to 0.6 cm. Length: 0.5 cm to 0.6 cm. Width: 0.3 cm to 0.4 cm. Color: Yellow (RHS 9A) and dotted (RHS 174A/B).

*Reproductive organs*.—Column: Length: 7.0 mm to 9.0 mm. Diameter: 4.2 mm to 4.4 mm. Color: White (RHS NN155C). Pollinia: Quantity: 2. Diameter: 0.8 mm to 1.1 mm. Color: Yellow-orange (RHS 23A). Ovary: Length: 5.0 mm to 7.0 mm. Diameter: 1.9 mm to 2.1 mm. Pedicel: Length: 29.0 mm to 31.0 mm. Diameter: 2.1 mm to 2.3 mm. Color: Light green at the base (RHS 146A), white (RHS NN155C) and light purple (RHS 76D) towards the flower.

Disease, pest, and stress resistance: No specific resistance or susceptibility observed to pathogens and pests common to *Phalaenopsis*.

Fruit and seeds: Fruit and seed development has not been observed on plants of the new *Phalaenopsis*.

COMPARISON WITH PARENTAL AND COMMERCIAL VARIETIES

'PHALDRIDOP' differs from female parent plant '22819-01' (unpatented) by flower size and plant length. 'PHALDRIDOP' has narrower flowers and shorter plants than '22819-01'.

The male parent of 'PHALDRIDOP', cultivar '01-1696' (unpatented), is no longer in existence, so a meaningful comparison cannot be made.

'PHALDRIDOP' is most similar to the commercial *Phalaenopsis* plants named 'ANTWAREN' (unpatented) and 'PHALTULEN' (unpatented). 'PHALDRIDOP' differs from the commercial variety 'ANTWAREN' in that 'PHALDRIDOP' has lateral sepals that are evenly colored with no overcolor, whereas 'ANTWAREN' has lateral sepals that are dotted with light green overcolor. Additionally, 'PHALDRIDOP' has an apical lobe that is white and yellow, and a pedicel that is light green at the base with white and light purple towards the flower, whereas 'ANTWAREN' has an apical lobe that is white and yellow with brown at the base, and a pedicel that is light green at the base with white towards the flower.

'PHALDRIDOP' differs from the commercial variety 'PHALTULEN' in that 'PHALDRIDOP' has an apical lobe that is white and yellow and a medium curvature of the lateral lobe, whereas 'PHALTULEN' has an apical lobe that is white with green at the base and a strong curvature of the lateral lobe. Additionally, 'PHALDRIDOP' has a callus that is yellow and a pedicel that is light green at the base with white and light purple towards the flower, whereas 'PHALTULEN' has a callus that is green and yellow and a pedicel that is light green.

I claim:

1. A new and distinct variety of *Phalaenopsis* plant named 'PHALDRIDOP', substantially as described and illustrated herein.

* * * * *